Figure 1:
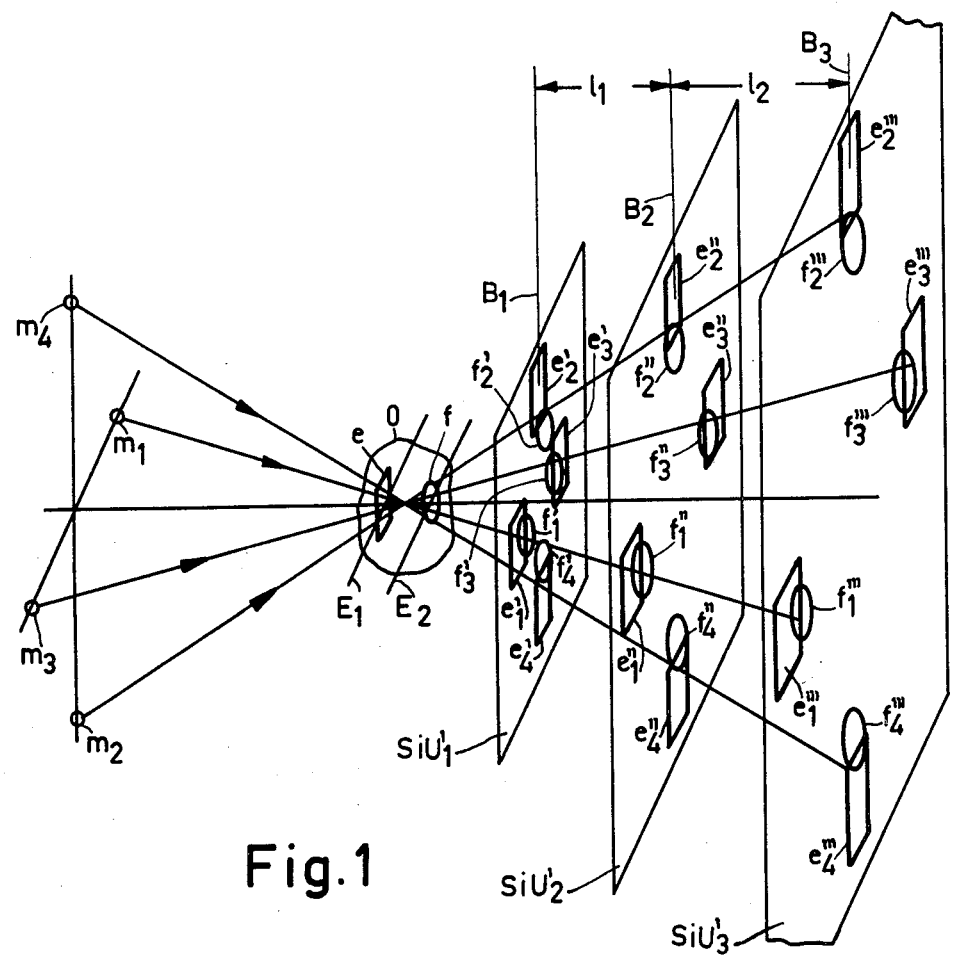

350-3.77
3/7/78    XR    4,078,177

United States Patent [19]
Tiemens

[11] 4,078,177
[45] Mar. 7, 1978

[54] LAYER-WISE REPRODUCTION OF THREE-DIMENSIONAL OBJECTS BY SIMULTANEOUS SUPER-POSITION OF ENCODED IMAGES

[75] Inventor: Ulf Tiemens, Fahltskamp, Germany

[73] Assignee: U.S. Philips Corporation, New York, N.Y.

[21] Appl. No.: 673,259

[22] Filed: Apr. 2, 1976

[30] Foreign Application Priority Data

Apr. 5, 1975    Germany ............................... 2514988

[51] Int. Cl.$^2$ .......................... G03B 41/16; A61B 6/02
[52] U.S. Cl. ................................. 250/323; 250/445 T; 350/3.77
[58] Field of Search ............... 250/313, 314, 320, 323, 250/445 T; 350/3.5

[56] References Cited

U.S. PATENT DOCUMENTS 3,499,146   3/1970   Richards ........................ 250/445 T
3,818,220   6/1974   Richards ........................ 250/445 T
3,873,834   3/1975   Dammann et al. .............. 250/445 T

*Primary Examiner*—Ronald J. Stern
*Attorney, Agent, or Firm*—Frank R. Trifari

[57] ABSTRACT

A method of layer-wise reproduction of three-dimensional images by way of a number of simultaneously recorded, encoded superposition images of different image planes. The object is irradiated from different directions. Simultaneous-superposition images of the object are recorded in encoded form, by means of a large number of $m$ sources, from different directions in a number of $n$ planes which are situated one below the other. The decoding of these images for the layer-wise reproduction of the three-dimensional object is effected so that for each individual layer each of the $n$ simultaneous-superposition images, whose scale has been adapted relative to each other, is simultaneously or consecutively shifted and summed on a single recording medium a number of times which corresponds to the number of $m$ sources during the recording of the object.

12 Claims, 6 Drawing Figures

LAYER-WISE REPRODUCTION OF THREE-DIMENSIONAL OBJECTS BY SIMULTANEOUS SUPER-POSITION OF ENCODED IMAGES

The invention relates to a method of layer-wise reproduction of three-dimensional objects by way of a number of simultaneously recorded, encoded superposition images of different image planes, the object being irradiated from different directions.

Methods have been proposed whereby layers of an irradiated three-dimensional object can be decoded from a single encoded superposition image (U.S. patent application Ser. No. 558,016 filed Mar. 13, 1975, now U.S. Pat. No. 4,023,037, and German Patent publications Applications Nos. P 24 14 322.4, P 24 31 700.8, and P 24 32 595.9). These methods enable the three-dimensional reconstruction of an object by layer-wise reproduction. However, the signal-to-noise ratio is then comparatively unfavourable.

The invention has for its object to decode a number of $n$ simultaneously recorded superposition images of an object so that a layer of the three-dimensional image to be synthesized may be selected at random, the signal-to-noise ratio being improved at the same time.

The object is achieved in that superposition images of the object are recorded in encoded form by means of a large number of $m$ sources from different directions in a number of $n$ planes which are situated one below the other, the decoding of these images for the layer-wise reproduction of the three-dimensional object being so that for each individual layer each of the $n$ simultaneous-superposition images, whose scale has been adapted relative to each other, is shifted, simultaneously or consecutively, and summed on a single recording medium a number of times corresponding to the number of $m$ sources during the recording of the object.

Because a number of $n$ superposition images which are situated one below the other at a given distance from each other are simultaneously recorded, a source distribution which is favourable for the decoding is also feasible. A suitable source distribution is, for example, a statistic or non-redundant distribution as described by M. J. E. Colay in "Journal of the Optical Society of America", Volume 61, page 272, 1971. For the decoding the superposition images, a mathematical property of these distributions is utilized, i.e. the fact that the autocorrelation function thereof approximates a Delta function according to Dirac.

The method can be used for medical X-ray diagnosis, notably for the display of moving three-dimensional objects, such as the beating heart which moves quickly. The moving object is then simultaneously exposed by different X-ray tubes from different positions and recorded on X-ray films, arranged one below the other, in accordance with the consecutive exposure technique and is subsequently decoded in all layers using the method according to the invention after development of the films.

The device according to the invention can be utilized particularly advantageously in combination with a holographic-optical method of making layer images as described in German Patent publication No. P 24 19 259.4. The primary images from different directions required are then replaced by the obtained synthesized perspective images. It is thus possible to combine the advantages of both devices.

Whilst the method according to the invention produces perspective images from a number of simultaneous superposition images recorded in a described phase according to the consecutive exposure technique, the holographic-optical method can produce, by means of suitable optical components, layers at an arbitrary depth and location and also inclined layers within the object continuously well-focussed on a stationary screen; when use is made of spatially coherent light in the Fourier plane of a suitable objective, the spatial Fourier transform of the transmitted layer image can thus also be produced.

Instead of the recording of $m$ different perspective images assigned to $m$ recording directions, it is alternatively possible, by shifting and summing each time $n$ simultaneous-superposition images, to use a sequential decoding of the individual simultaneous-superposition images each time for the same layer of the object, the decoding being effected by means of a point hologram made by means of a flat reference beam and the illumination of a hole mask in the convergent beam (see also U.S. patent application Ser. No. 558,016). The separately decoded layer images can also be summed to form an overall layer image.

The simultaneous-superposition images are obtained in that an object is simultaneously or consecutively irradiated from $m$ spatially separated X-ray sources, the projections being simultaneously stored on $n$ recording materials which are arranged one below the other at the same distance from each other. Each of the $n$ simultaneous-superposition images contains the information of the three-dimensional object recorded by a large number of sources from different directions from which the object is irradiated. The location of the individual images relative to each other within the superposition images differs in the $n$ simultaneous-superposition images; this is utilized to obtain a blurring effect during the summing of the simultaneous-superposition images so as to form a synthesized perspective image.

Each individual image of the $n$ simultaneous-superposition images can be decoded in accordance with the said method.

The simultaneous-superposition images are made during an initial phase. In this method a three-dimensional object is irradiated, simultaneously or consecutively, from $m$ different directions and is recorded in the form of $n$ simultaneous-superposition images on a number of $n$ record carriers which are arranged one below the other. For the simultaneous recording of different simultaneous-superposition images, use can be effectively made of a simultaneous layer device in combination with a film foil arrangement as available for the usual tomography apparatus.

Because scale of the $n$ simultaneous-superposition images relative to each other differs in accordance with their position in the layer device, the scales are adapted, i.e., normalized or equalized in sizes to each other during a second phase.

During a third phase the first summing operation takes place of the $n$ simultaneous-superposition images having the same scale, so that $m$ synthesized perspective images are obtained. To this end, the $n$ superposition images are arranged one above the other and summed so that only the images recorded by *one* of the $m$ different sources coincide. In the perspective image thus produced, the image recorded from a single direction appears to be well-focussed, whilst all other images are blurred.

Subsequently, the $n$ simultaneous-superposition images are again summed in the described manner so that the image from an other direction is well focussed, etc. Thus, a number of $m$ perspective images is obtained which corresponds to the number of sources used for the encoding.

When use is made of a non-redundant distribution of $m$ point sources, the first summing operation produces *one* projection image from one direction having the amplitude $n$, surrounded by $m$-1 blurred figures which consist in total of $n \cdot (m-1)$ projection images from all other directions having the amplitude 1.

During a fourth phase a second summing operation is effected, i.e. the summing of $m$ perspective images so as to form layer images. The layer depth, corresponding to a given shift of the individual images relative to each other, can then be chosen at random.

$n$-times superposition of the $m$ perspective images and simultaneously a shift which corresponds to the depth of the layer produces *one* image of the desired layer having the amplitude $m \cdot n$ and, moreover, $m$ secondary images of the amplitude $n$ which contain the information of the other layers and which do not contain any information concerning the layer produced, and also $n \cdot (m-1)$ blurred figures which again consist of in total $m \cdot n(m-1)$ projection images from all other directions having the amplitude. 1.

The $m$ secondary images in the layer image are optimally blurred by way of the non-redundant distribution of the sources, whilst the $m \cdot n(m-1)$ projection images have a negligibly small amplitude of 1 during the second summing operation and are almost completely suppressed.

Some preferred embodiments in accordance with the invention will be described in detail hereinafter.

Figure 4:
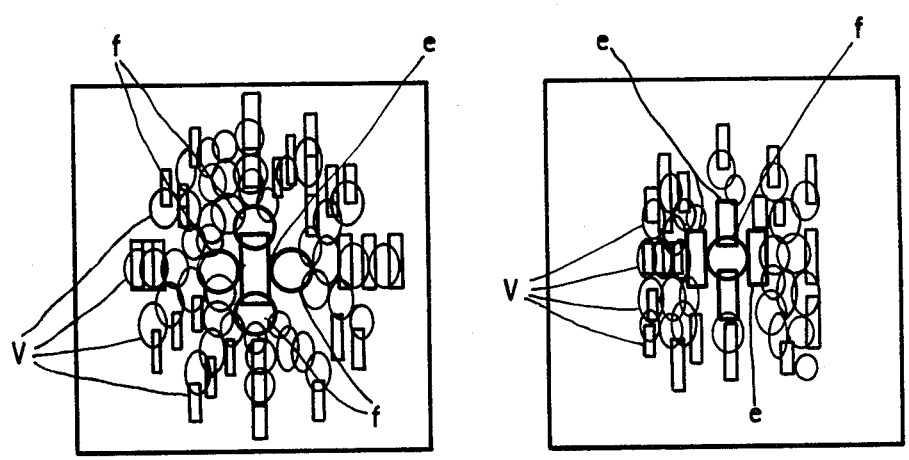
Figure 2:
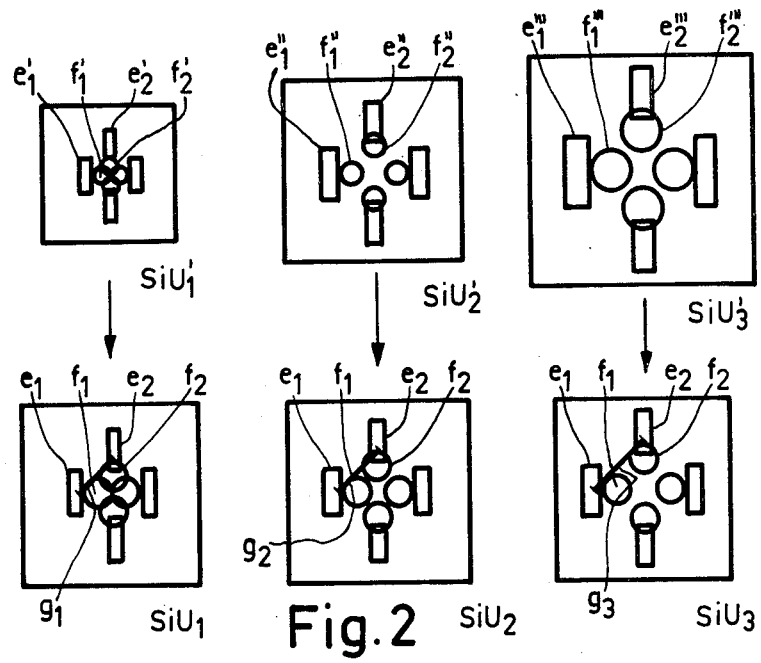
Figure 3:
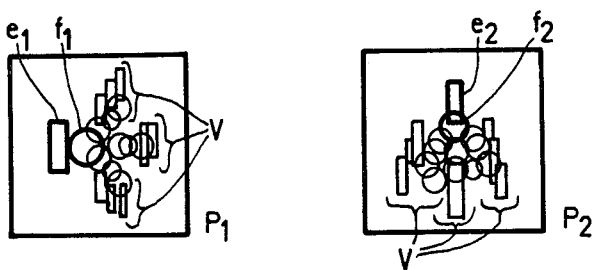
Figure 5:
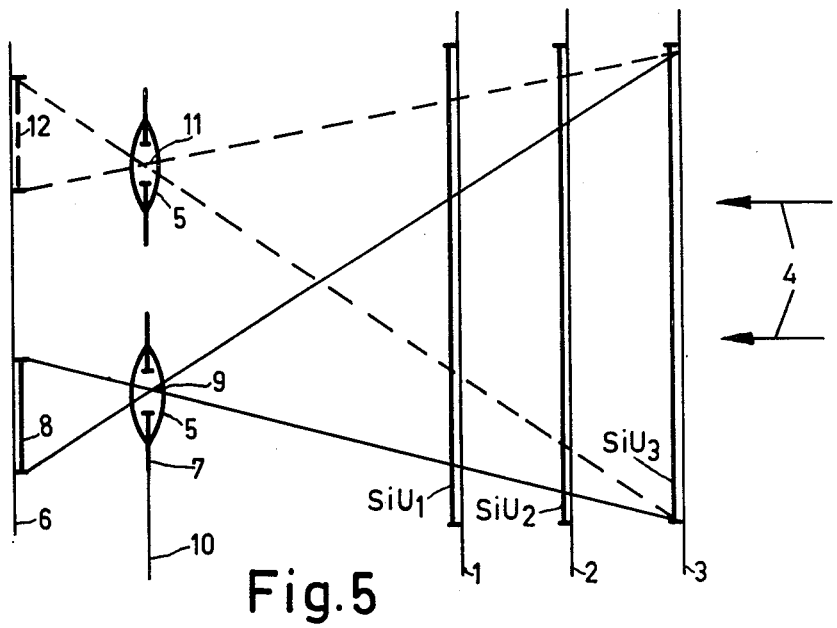
Figure 6:
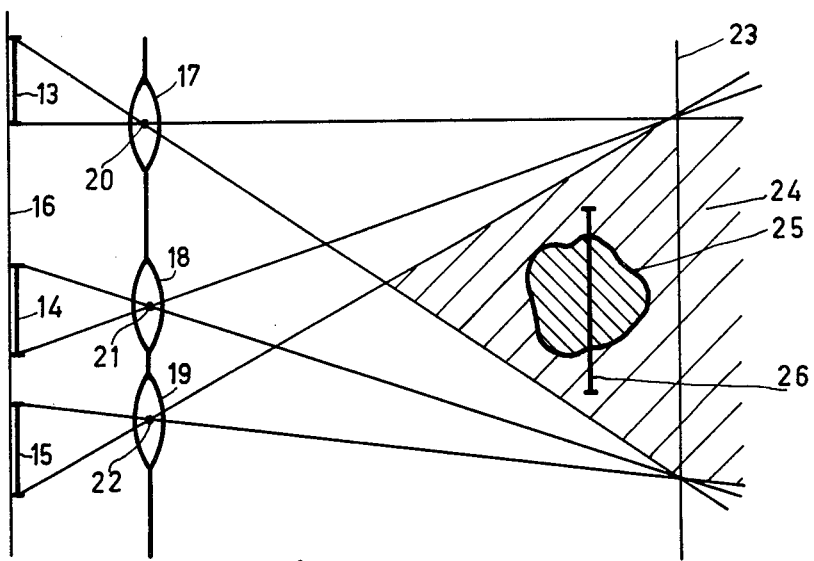

FIG. 1 diagrammatically shows the recording of the simultaneous-superposition images, FIG. 2 shows the scale adaptation of the simultaneous-superposition images, FIG. 3 shows the formation of the synthesized perspective images, FIG. 4 shows the formation of the layer images, FIG. 5 diagrammatically shows an optical arrangement for the formation of perspective images, and FIG. 6 diagrammatically shows an arrangement for forming a three-dimensional real image of the object.

The method will be described in simplified form, taking into account only $m = 4$ recording positions for the formation of only $n = 3$ simultaneous-superposition images. The extension to more than four directions and more than three simultaneous-superposition images will be obvious.

FIG. 1 shows the recording of the $n$ simultaneous-superposition images. The object O is irradiated by means of a source distribution $m_1 - m_4$, for example, four X-ray tubes. For further simplification, only two planes $E_1$ and $E_2$, having the symbols $e$ and $f$, are considered. In the three image planes $B_1$, $B_2$ and $B_3$, at the distances $l_1$ and $l_2$, the superposition images $S_iU_1'$, $S_iU_2'$ and $S_iU_3'$ are formed in which the two planes $E_1$ and $E_2$ of the object O are each imaged four-fold. The simultaneous-superposition image $S_iU_1'$ contains the images $e_1'f_1'$; $e_2'f_2'$; $e_3'f_3'$ and $e_4'f_4'$; the image $S_iU_2'$ contains $e_1''f_1''$; $e_2''f_2''$; $e_3''f_3''$ and $e_4''f_4''$; and the image $S_iU_3'$ contains: $e_1'''f_1'''$; $e_2'''f_2'''$; $e_3'''f_3'''$ and $e_4'''f_4'''$.

Because the individual simultaneous-superposition images have a different scale, due to the distances $l_1$ and $l_2$, when this recording technique is used, the scales must be compensated for as shown in FIG. 2. It is important that the scale of the images of $e$ and $f$ which differs from superposition image to superposition image is equalized. This can be effected geometrically-optically by the use of a suitable objective lens, wherein the imaging ratio for the individual simultaneous-superposition images are adopted or selected in accordance with the difference in scale. The images $e_1'f_1'$, $e_2'f_2'$ in $S_iU_1'$; $e_1''f_1''$, $e_2''f_2''$ in $S_iU_2'$ and $e_1'''f_1'''$, $e_2'''f_3'''$ are adapted to $e_1f_1$ and $e_2f_2$ in the images $S_iU_1$, $S_iU_2$ and $S_iU_3$. It is thus achieved that the scale of the individual images is equal, but the distance $g_1$, $g_2$ and $g_3$ of the images $e_1f_1$ and $e_2f_2$ changes relative to each other.

It is thus possible to obtain a synthesized perspective image as illustrated in FIG. 3. The three simultaneous-superposition images $S_iU_1$-$S_iU_3$ are summed i.e., aligned, so that each time an image, for example, $e_1f_1$, coincides in the image $P_1$, whilst all other images V are shown to be linearly blurred. After three further summing operations, using the same simultaneous-superposition images, the perspective images $P_2$, $P_3$ and $P_4$ with the focussed images $e_2f_2$, $e_3f_3$ and $e_4f_4$ are obtained.

FIG. 4 shows the formation of the layer images from the perspective images. In order to reproduce a given plane of the object O in FIG. 2, for example, the plane $E_1$ having the symbol $e$, as a layer image, the perspective images $P_1 - P_4$ are summed in a shifted manner relative to each other so that the symbols $e_1 - e_4$ coincide and that ultimately the layer image $e$ appears with maximum amplitude, whilst all other details of the associated images, for example, $f_1 - f_4$, of mean amplitude are optimally blurred by way of the non-redundant source distribution. Moreover, the layer image contains all other perspective images V which are present within the blurred figures in the perspective images and which appear as a background of minimum amplitude.

FIG. 5 diagrammatically shows a feasible embodiment of a device for forming perspective images, the otherwise used scale adaptation being omitted therein. The simultaneous-superposition images $S_iU_1$ to $S_iU_3$ (FIG. 1) are situated in the original planes 1, 2 and 3 which correspond to the planes $P_1$, $P_2$ and $P_3$ of FIG. 1 and are illuminated from the rear. By means of a suitable objective 5, at the same time all $n$ simultaneous-superposition images ($S_iU_1$, $S_iU_2$, $S_iU_3$) are images in the image plane 6. In order to obtain adequate depth of focus, a diaphragm 7 is used so that the image 8 is a superposition of all simultaneous-superposition images. If the position 9 of the objective corresponds, for example, to the position $m_2$ in FIG. 1, 8 will be synthesized perspective image for the direction $m_2$. When the objective 5 is shifted in the plane 10 to an arbitrary position $m$ which corresponds to the direction of an other source of the source distribution during the recording of simultaneous-superposition images, a further synthesized perspective image for the corresponding direction is obtained.

FIG. 6 shows how a three-dimensional real image of the object can be reconstructed by means of the synthesized perspective images. The perspective images 13, 14 and 15 in the plane 16 are simultaneously imaged in the plane 23 by means of lenses 17, 18 and 19 whose positions 20, 21 and 22 corresponds to the recording positions during the formation of the simultaneous-superposition images. When the depth of focus of the lenses 17, 18 and 19 is adequate, the real image of the recorded object appears in the superposition region 24 of the images. This image can be registered by means of a detector 26, for example, a frosted glass plate.

What is claimed is:

1. A method for producing layer-wise images of three-dimensional objects comprising:

irradiating said objects in different directions from $m$ points to record images of said object in each of a plurality of $n$ of spaced apart planes, whereby each source contributes to the image recorded in each plane, to produce $m$ superposition images, $m$ and $n$ being integers, equalizing the scale of said superposition images and aligning said superposition images $m$ times to separately optically align portions thereof corresponding to the image produced by separate ones of said sources, to thereby produce $m$ perspective images, and aligning said $m$ perspective images with respect to features of a given plane of said object to produce a layer image.

2. The method of claim 1, wherein said step of aligning superposition images comprises shifting the relative physical alignment of said superposition images.

3. The method of claim 1, wherein said step of aligning perspective images comprises shifting the relative physical alignment of said perspective images.

4. The method of claim 1, wherein said step of aligning superposition images comprises optically aligning said portions of said superposition images.

5. The method of claim 1, wherein said step of aligning perspective images comprises optically aligning said perspective images.

6. The method of claim 1, comprising recording said superposition images to produce synthesized superposition images.

7. The method of claim 1, comprising recording said perspective images.

8. The method of claim 1, comprising imaging said perspective images on a frosted glass plate.

9. The method of claim 1, further comprising recording said $m$ perspective images to produce $m$ synthesized perspective images each of which image the information in focus from one direction and blur information from all other directions.

10. The method of claim 1, wherein said step of equalizing the scale of images comprises geometrically-optically imaging said superposition images in accordance with their differences in the scale.

11. The method of claim 1, wherein each of said $m$ perspective images is imaged by simultaneously projecting all of the superposition images in their original position by means of an objective lens while maintaining the original recording geometry, the position of the objective lenses during projection of said superposition images corresponding to the position of the source for which the relevant perspective image is synthesized.

12. The method of claim 1, wherein said $m$ perspective images are simultaneously projected in the original object plane from $n$ directions, corresponding to the recording positions during the formation of the $m$ superposition images, by means of $m$ lenses, the superposition of all $m$ perspective images producing a three-dimensional real image of the object which can be layered by means of a detector surface.

* * * * *